(12) United States Patent
Linnenkohl et al.

(10) Patent No.: US 8,400,503 B2
(45) Date of Patent: Mar. 19, 2013

(54) METHOD AND APPARATUS FOR AUTOMATIC APPLICATION AND MONITORING OF A STRUCTURE TO BE APPLIED ONTO A SUBSTRATE

(75) Inventors: Jan Anders Linnenkohl, Bensheim (DE); Andreas Tomtschko, Winnsburg (DE); Mirko Berger, München (DE); Roman Raab, München (DE)

(73) Assignee: Quiss GmbH (DE)

( * ) Notice: Subject to any disclaimer, the term of this patent is extended or adjusted under 35 U.S.C. 154(b) by 1515 days.

(21) Appl. No.: 10/584,120

(22) PCT Filed: Jul. 16, 2004

(86) PCT No.: PCT/EP2004/007964
§ 371 (c)(1),
(2), (4) Date: Jun. 29, 2007

(87) PCT Pub. No.: WO2005/065844
PCT Pub. Date: Jul. 21, 2005

(65) Prior Publication Data
US 2008/0024602 A1  Jan. 31, 2008

(30) Foreign Application Priority Data

Dec. 23, 2003 (DE) .................................. 103 61 018

(51) Int. Cl.
*H04N 9/47* (2006.01)
*G06K 9/00* (2006.01)

(52) U.S. Cl. ........ 348/125; 348/126; 348/127; 348/128; 348/129; 348/130; 382/141; 382/142; 382/143; 382/144; 382/145

(58) Field of Classification Search .......... 348/125–134; 382/141–152
See application file for complete search history.

(56) References Cited

U.S. PATENT DOCUMENTS

| | | | |
|---|---|---|---|
| 3,742,901 A | 7/1973 | Johnston | |
| 4,575,304 A | 3/1986 | Nakagawa et al. | |
| 4,576,482 A * | 3/1986 | Pryor | 356/612 |
| 4,628,464 A * | 12/1986 | McConnell | 382/153 |
| 4,666,732 A | 5/1987 | Schucker | |
| 4,724,302 A * | 2/1988 | Penney et al. | 219/130.21 |
| 4,849,679 A * | 7/1989 | Taft et al. | 318/577 |
| 4,916,286 A | 4/1990 | Sarugaku et al. | |
| 4,969,199 A * | 11/1990 | Nara | 382/146 |
| 4,998,502 A | 3/1991 | Schucker | |
| 5,110,615 A | 5/1992 | Maiorca et al. | |
| 5,402,351 A * | 3/1995 | Batchelder et al. | 700/119 |

(Continued)

FOREIGN PATENT DOCUMENTS

| | | |
|---|---|---|
| DE | 3243341 A1 | 6/1983 |
| DE | 3506110 A1 | 9/1986 |

(Continued)

*Primary Examiner* — Chikaodili E Anyikire
(74) *Attorney, Agent, or Firm* — Brooks Kushman P.C.

(57) ABSTRACT

A method and apparatus are provided for automatic application and monitoring of a structure to be applied onto substrate. A plurality of cameras positioned around an application facility are utilized to monitor the automatic application of a structure on a substrate by means of a stereometry procedure. Three-dimensional recognition of a reference contour position results in the overlapping area to be used for gross adjustment of the application facility prior to applying the structure.

45 Claims, 12 Drawing Sheets

U.S. PATENT DOCUMENTS

| | | | |
|---|---|---|---|
| 5,429,682 A | 7/1995 | Harlow, Jr. et al. | |
| 5,510,149 A | 4/1996 | Schucker | |
| 5,532,452 A | 7/1996 | Lechner et al. | |
| 5,533,146 A | 7/1996 | Iwai | |
| 5,572,102 A | 11/1996 | Goodfellow et al. | |
| 5,807,449 A | 9/1998 | Hooker et al. | |
| 5,878,151 A * | 3/1999 | Tang et al. | 382/103 |
| 5,932,062 A | 8/1999 | Manser | |
| 5,937,143 A | 8/1999 | Watanabe et al. | |
| 5,959,425 A | 9/1999 | Bieman et al. | |
| 6,064,429 A * | 5/2000 | Belk et al. | 348/128 |
| 6,064,759 A * | 5/2000 | Buckley et al. | 382/154 |
| 6,356,299 B1 * | 3/2002 | Trosino et al. | 348/128 |
| 6,541,757 B2 * | 4/2003 | Bieman et al. | 250/221 |
| 6,763,284 B2 | 7/2004 | Watanabe et al. | |
| 7,112,246 B2 | 9/2006 | Schucker | |
| 7,177,459 B1 * | 2/2007 | Watanabe et al. | 382/151 |
| 7,577,285 B2 * | 8/2009 | Schwarz et al. | 382/141 |
| 7,945,349 B2 | 5/2011 | Svensson et al. | |
| 8,116,928 B2 | 2/2012 | Wu et al. | |
| 8,137,738 B2 | 3/2012 | Linnenkohl et al. | |
| 2003/0043116 A1 * | 3/2003 | Morrison et al. | 345/158 |
| 2003/0078694 A1 | 4/2003 | Watanabe et al. | |
| 2004/0011284 A1 | 1/2004 | Schucker | |
| 2005/0027399 A1 | 2/2005 | Koh et al. | |
| 2005/0251290 A1 | 11/2005 | Skourup et al. | |
| 2005/0259245 A1 * | 11/2005 | Cemic et al. | 356/237.2 |
| 2006/0147103 A1 | 7/2006 | Linnenkohl et al. | |
| 2007/0292629 A1 | 12/2007 | Linnenkohl et al. | |
| 2010/0042319 A1 | 2/2010 | Wu et al. | |
| 2010/0152944 A1 | 6/2010 | Kouno et al. | |
| 2011/0106311 A1 | 5/2011 | Nakajima et al. | |
| 2011/0282492 A1 | 11/2011 | Krause et al. | |
| 2012/0039524 A1 | 2/2012 | Linnenkohl et al. | |

FOREIGN PATENT DOCUMENTS

| | | |
|---|---|---|
| DE | 268049 A1 | 5/1989 |
| DE | 69103951 T3 | 10/1997 |
| DE | 69410684 T2 | 12/1998 |
| DE | 19852079 A1 | 5/2000 |
| DE | 100 48 749 A1 | 11/2002 |
| EP | 0203803 A1 | 12/1986 |
| EP | 0576498 A1 | 1/1994 |
| FR | 2741438 A1 | 5/1997 |
| FR | 2817618 A1 | 6/2002 |
| JP | 2277573 A | 11/1990 |
| WO | 0226397 A1 | 4/2002 |
| WO | 2005063406 A1 | 7/2005 |

* cited by examiner

METHOD AND APPARATUS FOR AUTOMATIC APPLICATION AND MONITORING OF A STRUCTURE TO BE APPLIED ONTO A SUBSTRATE

The present application relates to and claims priority from European Application Serial No. PCT/EP2004/007964 filed Jul. 16, 2004, titled "METHOD FOR AUTOMATIC APPLICATION AND MONITORING OF A STRUCTURE TO BE ADDLIED ONTO A SUBSTRATE, AND DEVICE THEREFORE", the complete subject matter of which is hereby expressly incorporated in its entirety.

The present invention relates to a method for automatic application and monitoring of a structure to be applied onto a substrate, and a corresponding apparatus.

For automatic application and monitoring of a structure to be applied onto a substrate, it has been customary to carry out optical measurements. For automatic application and monitoring of a structure, frequently various systems for fully automatic testing of the structure, including adhesive and sealing agent lines are used. For this purpose, multiple video cameras are directed at the structure to be recognized, whereby, in addition, an illumination module serving to generate a contrast-rich camera image is required.

In order to be able to monitor an adhesive line or adhesive trail while it is being applied, it is necessary to teach-in a reference adhesive trail (i.e., to have the camera or cameras scan the reference adhesive trail) in order to calculate corresponding parameters on which the assessment of the applied adhesive trails is subsequently based.

However, individual components are not always supplied to the same position of the application facility or the apparatus for automatic application and monitoring by means of the supplier of the technology. Moreover, application of an adhesive trail to a fold or joining seam requires correction of the tolerances of the individual components or correction of the position of the individual joining seams or folds.

Moreover, there is a need for a method for automatic application and monitoring of a structure to be applied onto a substrate, preferably an adhesive agent trail and/or an adhesive trail. In addition, the application structure and/or adhesive trail is monitored at a high accuracy while it is being applied.

It is therefore the object of the present invention to provide a method for automatic application and monitoring of a structure to be applied onto a substrate. The application structure and/or adhesive trail is monitored at a high accuracy while it is being applied. Automatic control of the application facility, or positional correction—with regard to positional tolerances of the individual components and/or tolerances of the joining seams or similar structures—is facilitated.

Moreover, it is an object of the present invention to provide a suitable apparatus for carrying out the method according to the invention.

According to the invention, a method for automatic application and monitoring of an adhesive trail onto a substrate or component, in particular a fold or joining seam, is proposed. A reference edge or a reference seam is determined by a first camera, in a leading direction of the application facility, in order to control or regulate the application facility according to the reference edge. Simultaneously or directly after applying the adhesive trail onto the substrate or the fold or location where components abut, a second camera carries out online monitoring of the applied adhesive trail in a trailing direction (i.e. the adhesive trail is applied onto the substrate and then the second camera checks the quality of the adhesive trail that was just applied). According to the invention, control or regulation of the application facility according to the reference edge facilitates concurrent seam application guidance for two components to be glued together and online monitoring of adhesive application and/or sealing agent application. Thus, a reduction of the sealing agent applied is achieved, because the seam application guidance and simultaneous control necessitate the use of less material due to the compensation of tolerances.

Accordingly, for a three-dimensional positional correction with regard to positional tolerances of the individual components or tolerances of joining seams, it is advantageous for the reference contour or a feature to be determined by at least two cameras. The two cameras carry out a three-dimensional positional correction for the application facility by means of the stereometry procedure.

It is also advantageous if the two cameras record the substrate, a section of the component or one or more components in the form of a full image or a large image, whereby the full images or large images of the two cameras comprise an overlapping area in a leading direction. The three-dimensional recognition of reference contour position results in the overlapping area to be used for gross adjustment of the application facility prior to applying the structure. In this context, corresponding correction values are transmitted to the application facility or to a robot in order to shift the robot's coordinant system for the application of the adhesive agent.

If a projection is made onto the area of the reference contour (e.g., if one or more laser lines are applied onto the substrate in the form of a projection) then a three-dimensional analysis of the profile with regard to the height and contour of arbitrary components can be facilitated. Even though the reference contour is not analyzable by common image processing without an additional projection.

Moreover, a particular advantage is if the reference contour is determined by a first camera in a leading direction to regulate the progression of the structure to be applied according to the reference contour. The first camera records a strip of the image for online regulation of the application of the adhesive structure. By means of this partial scan or partial read-out of the image recording chip, only small data streams need to be processed such that the image recording rate can be increased several-fold. In this context, the images are recorded at defined fixed time intervals and are independent of the speed of the application facility or the robot speed.

If the second camera uses just a strip of the image for online monitoring of the applied structure, the adhesive application can proceed at a higher speed. The seam application guidance can proceed at a higher speed in an online fashion because both cameras facilitate high-frequency image recording and rapid analysis with just one sensor with two cameras. In this context, a reference edge is determined in a leading direction parallel to the online inspection of the track applied sealing agent. Difference values are transmitted to the robot for correction of the track such that the accuracy of the application of the sealing agent can be significantly and a reduction of the material needed is attained. Due to this only partial read-out of the image recording chip of the individual cameras, images of all cameras can be captured synchronously, in parallel, and simultaneously.

According to an advantageous embodiment, the strips of the images of the cameras are recorded to form a single sequence of images. The image recording rate is increased in line with the data reduction achieved by recording a strip of the image in order to increase the speed of the automatic application and monitoring of the sealing agent application. By storing a single sequence of images for all the cameras, the respective images of the individual cameras can be assigned according to the travel of the application facility as a function of location.

If each camera uses only a part, in particular approximately a third, fourth or fifth, of the picture lines as a strip of the image, the image recording rate is multiplied accordingly. In particular, the image recording rate is multiplied essentially three-fold, four-fold or five-fold.

Moreover, it is advantageous for a parameterization and a recording of the application track to proceed in a single image recording run, whereby the images of all cameras are stored in a sequence of images.

According to the invention, the stored sequence of images use the robot travel path, the robot travel time, the robot coordinates as well as the position, the contrast, the gray scale value, color value, the width, and the quality of the applied structure for parameterization.

Because only a small amount of data has to be included in the parameterization calculation and because of the high image recording rate, recording comparably short partial sections of the sealing agent application and of the reference contour or joining seam (e.g., between 1 mm and 3 mm in length) is feasible. Moreover, it is advantageous to store the structure to be applied by parameterization essentially in the form of a vector chain. A high image recording rate and short partial sections of essentially between 0.5 mm and 4 mm, in particular between 1 and 3 mm, are used. The vectorization is advantageous in that the adhesive trail in the form of a vector chain can be stored in a camera-transcending global coordinate system. In contrast, traditionally, only a local camera image-oriented coordinate system is being used. The invention thus facilitates that a switch of the sensor head only necessitates recalibration or new calibration without having to teach-in the adhesive trail again.

According to another advantageous embodiment, an advantage is to use three cameras, whereby each camera is used or can be used both for regulation in leading direction according to the reference contour and for monitoring of the applied structure in a trailing direction. The three cameras each comprise an overlapping area to the adjacent camera on a circular line. As a result, a sensor with three cameras can be attached to be fixed on the application facility, since each individual camera can assume both the regulation of seam application guidance and online monitoring of sealing agent application. Advantageously, the angle values of the circular line from 0° to 360° form a global coordinate system. A segment of the circular line is assigned to the images of the individual cameras in order to carry out on the circular line either the seam application guidance or the monitoring of the sealing agent. As a result, two of the three cameras are always active for analysis, i.e. one for seam application guidance and one other for the monitoring of sealing agent application.

Another advantage is that an automatic switch is made, when the reference contour or the adhesive trail progresses from one camera to the next camera. For example, the activation is transferred from the one camera to the other camera when the application structure or the reference contour progresses from the segment of the circular line of the one camera via the overlapping area to the segment of the circular line of another camera.

Since the images are recorded very shortly one after the other (e.g., every 0.5 to 4 mm; in particular, 1 to 3 mm), it can be assumed that the position of the adhesive trail or joining edge cannot change too strongly, which significantly improves the significance and/or reliability of the a priori knowledge such that the location of the track can be predicted. One positive effect of such a priori knowledge is that the computer can recognize fully automatically the position of the track even in the absence of the expert knowledge of a human being, since the computer already knows approximately where the track will be progressing in the next image. This allows the search area to be reduced and the speed of analysis to be increased.

According to the present invention an apparatus is provided for automatic application and monitoring of a structure to be applied onto a substrate, preferably an adhesive line or adhesive trail, for carrying out the method according to the invention. At least one illumination module and one sensor unit are provided. The sensor unit is made up of at least two cameras that are provided around an application facility for applying the structure to be applied onto the substrate and are arranged on the application facility such that at least one camera is provided in a leading direction for regulation of the application facility by means of a reference contour and at least one camera is provided in a trailing direction for simultaneous online monitoring of the structure applied onto the substrate. The apparatus, according to the invention, can therefore be used, for example, to guide a seam as a reference contour for the control of the application facility or robot control. The apparatus can simultaneously carry out an online control of sealing agent application, such that less material is used in sealing agent application since the width of the adhesive agent track can be reduced due to the guidance of the application facility.

If the optical axes of the individual cameras essentially intersect, in the direction of view (e.g. the axial longitudinal axis of the application facility); or if the optical axes of the individual cameras are directed to be parallel to each other (e.g., in particular are directed to be perpendicular to the substrate) an advantage according to a development of this type is that a narrow area around the application facility can be monitored at a suitable resolution and a high image recording rate.

According to a preferred embodiment, the individual cameras, in particular 3 cameras, are arranged at equal distances from each other in the direction of the circumference.

Advantageously, the individual cameras interact with each other such that the images of the cameras are stored in a sequence of images, whereby these images are composed by the software from the three partial sections of the individual cameras that were recorded synchronously and captured in parallel.

If a projection facility projecting one or more features, in particular strips, onto the substrate for the three-dimensional analysis is provided on the application facility, arbitrary components can be used for correction or adjustment of the application facility prior to applying the structure.

According to a preferred embodiment, the projection facility emits one or more laser lines for a three-dimensional profile analysis. Arranging at least two projection facilities around the application facility facilitates a gap-free three-dimensional analysis around the application facility. The analysis of sealing agent height and sealing agent contour, as well as position and width, can be carried out according to the principle of triangulation by means of image processing.

According to a development of an invention, the cameras are arranged around the application facility. The cameras are arranged such that at least an essentially circular edge scan (e.g., in particular in the form of a circular caliper) is formed whose center is formed by the application facility of the structure. In this context, one or more circular calipers can be used that facilitate the determination of the edge of the adhesive trail on a circular line.

According to a preferred embodiment, the individual cameras comprise an overlapping area of 30° to 90° each, in particular essentially 60°, relative to the next camera. This overlapping area facilitates fully automatic switching between neighboring cameras when the adhesive trail progresses from the monitoring area of one camera to the monitoring area of the next camera. The selection of the camera is not bound to the robot position or to a time component, but rather always refers to the actual inspection results. For instance, the inspection results are based on the arrangement on the circular line of the circular caliper and/or the global coordinate system formed thereby.

Moreover, it is advantageous for the illumination module to be made up of light emitting diodes (LEDs), in particular infrared LEDs, ultra-violet LEDs (UV LEDs) or red-green-blue LEDs (RGB LEDs).

Moreover, one advantage is to use a calibrating disc with individual form elements for calibrating the individual cameras for the assignment of the angle assignment. The said form elements comprise, in particular, an angle distance of essentially 10°. This allows for assignment of the scaling factor, angle assignment, and center, as well as radius of the search circle for the individual cameras. According to the invention, the calibrating disc comprises at least three marker sites that are arranged in a circular arc of the calibrating disc of essentially 0°, 120°, and 240°, in order to calibrate three cameras.

Advantageous developments of the invention shall be illustrated in an exemplary fashion by means of the following drawings.

In the following, the design of the apparatus according to the invention for recognizing a structure to be applied onto a substrate is illustrated according to FIGS. 1 and 2.

Figure 1:
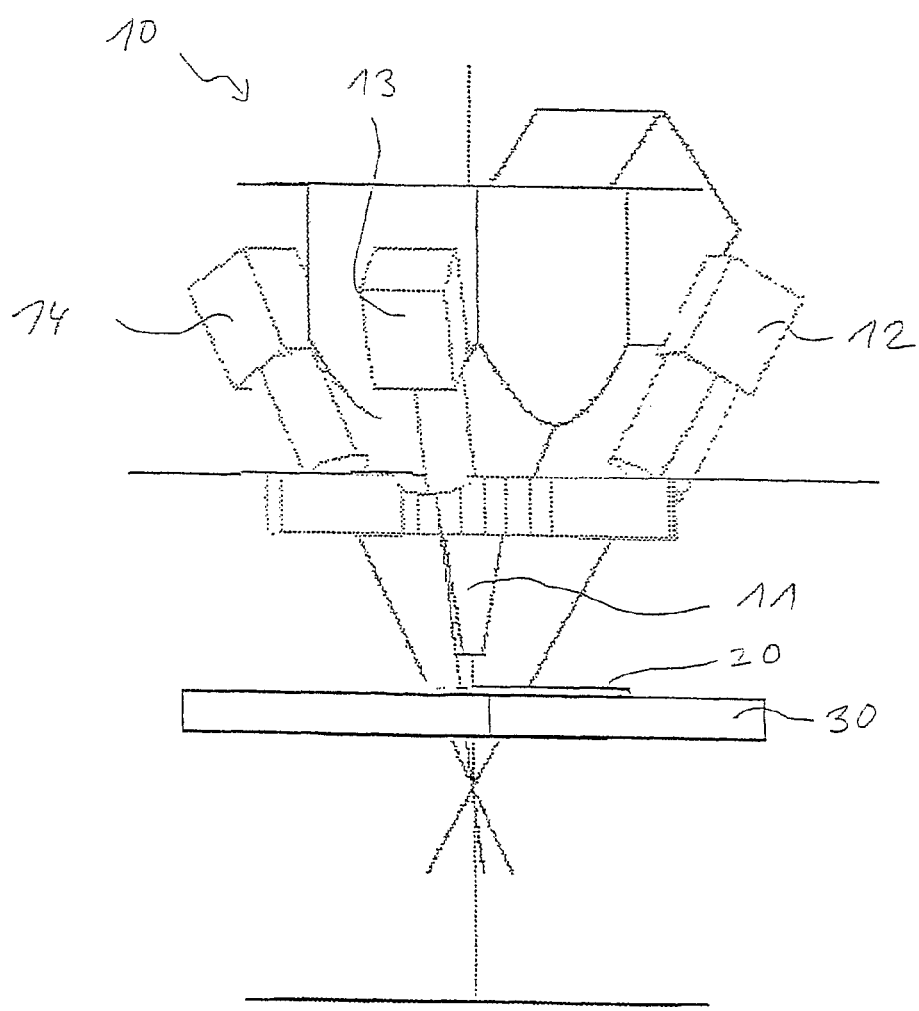
FIG. 1 shows a schematic side view of an apparatus according to the invention for application and monitoring of an adhesive trail.
Figure 2:
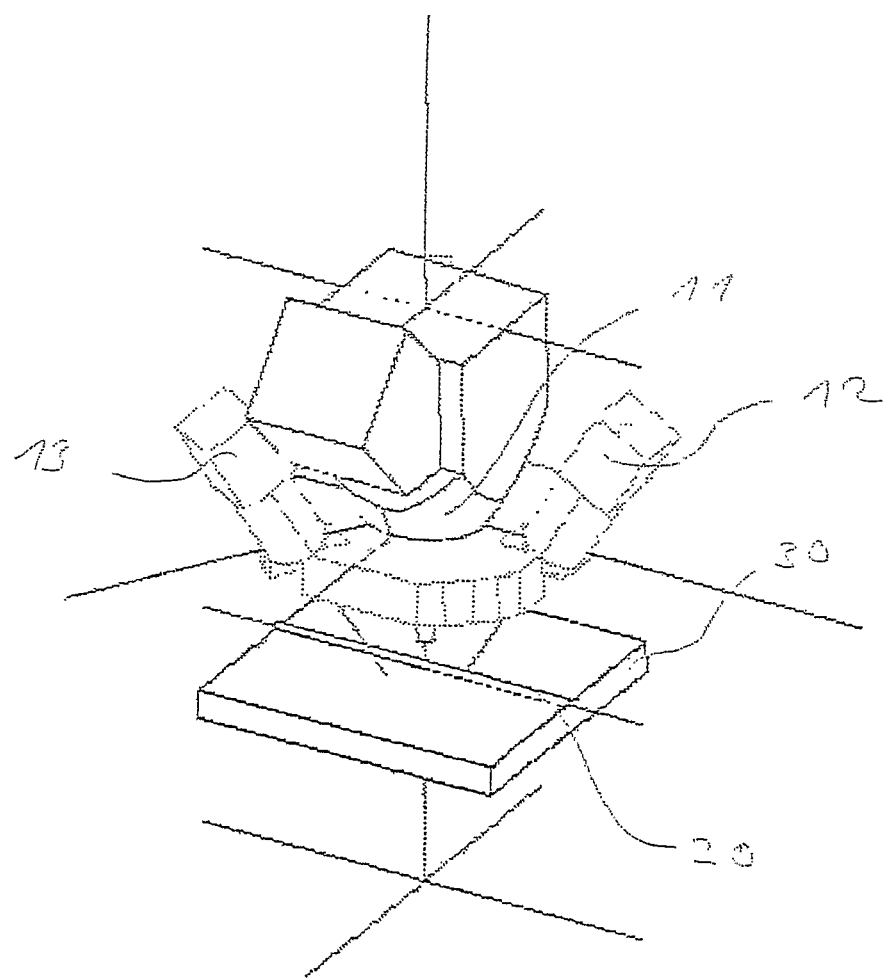
FIG. 2 shows a perspective view of the apparatus according to the invention of FIG. 1.

Reference number 10 indicates the schematically shown apparatus in FIG. 1 for application and monitoring of an adhesive trail. In the center of the apparatus, according to the invention, is arranged an application facility 11 by means of which an adhesive trail 20 is applied onto a substrate 30 or onto a sheet of metal 31 proceeding from right to left in FIG. 1. Three cameras 12, 13, 14 are arranged at equal distances from each other in a circle around the application facility 11. Each camera is directed at the application facility 11. As is evident from FIG. 1, the axial longitudinal axes of the three cameras 12, 13, 14 intersect the axial longitudinal axis of the application facility 11 just below the substrate 30. Thus, the focus of the individual cameras is arranged right around the area of the application facility 11, in particular, on a circular line.

In the inspection of the adhesive, either the application facility 11 with the cameras or the substrate 30 is moved. The adhesive trail 20 is simultaneously applied to the substrate 30 by means of the application facility 11 while the cameras 12, 13, and 14 monitor the applied structure. For the purpose of inspecting the adhesive, either the application facility 11 with the cameras or the substrate 30 is moved in order to apply the adhesive trail 20 onto the substrate 30 such as to follow a desired progression. In the method according to the invention, a first camera determines a reference contour, a reference line, or reference edge in a leading direction, as shown by camera 14 towards the left in FIG. 1. In order to regulate the progression of the structure to be applied, according to the reference contour, the images recorded by the first camera 14 are used to guide the application facility 11 in the application of the adhesive trail 20. The adhesive trail 20 is applied by the application facility 11 simultaneous to the determination of the reference contour. The application facility 11 is moved to the corresponding track and/or the corresponding adhesive trail progression according to the correction values determined by the first camera 14. Synchronous to this process, the adhesive application track is monitored by a second camera in a trailing direction. By this means, the cameras that are being moved along can control the adhesive trail 20, while the adhesive trail 20 is being applied, according to the reference contour independent of the travel path. The cameras monitor the quality of the adhesive trail 20 online. In FIG. 2, the adhesive trail 20 progresses from left to right which is shown as a continuous line. The desired progression of the adhesive trail 20 that can be applied to the metal sheet 31 and/or substrate 30 as reference contour (for example by laser or be embossed) is shown to the right of the application facility 11 by means of a dashed line.

Figure 3:
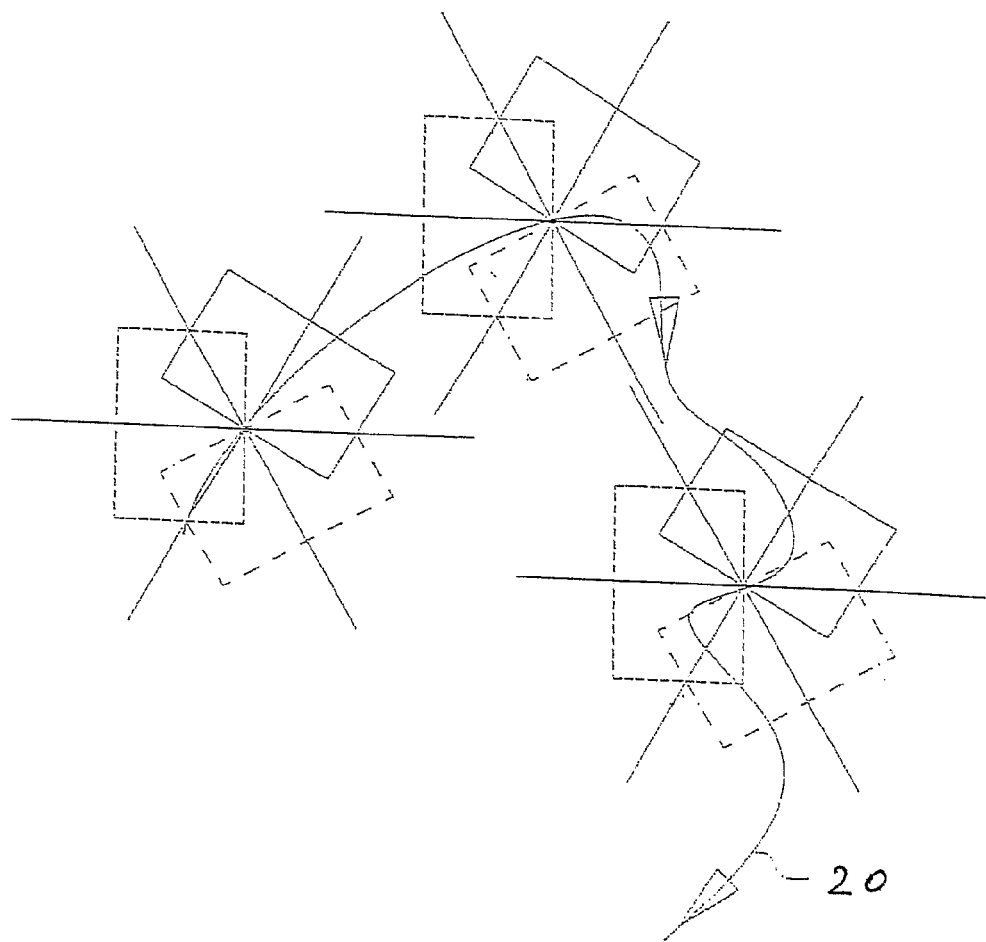
FIG. 3 shows the travel path of the apparatus according to the invention for application and monitoring of an adhesive trail.

FIG. 3 illustrates the progression of the adhesive trail 20 as indicated by arrows 21 and 22, whereby the direction or field of view 23, 24, and 25 of the three individual cameras 12, 13, and 14 is shown in three sites. The field of view 23, 24 and 25 of the three individual cameras 12, 13, and 14 are indicated by a rectangle drawn with a continuous line 23, a rectangle drawn with widely dashed lines 24, and a rectangle drawn with narrow dashed lines 25. As is evident from FIG. 3, the direction of the individual fields of view 23, 24 and 25 of the cameras remains constant at all times and only the whole apparatus is moved.

Figure 4:
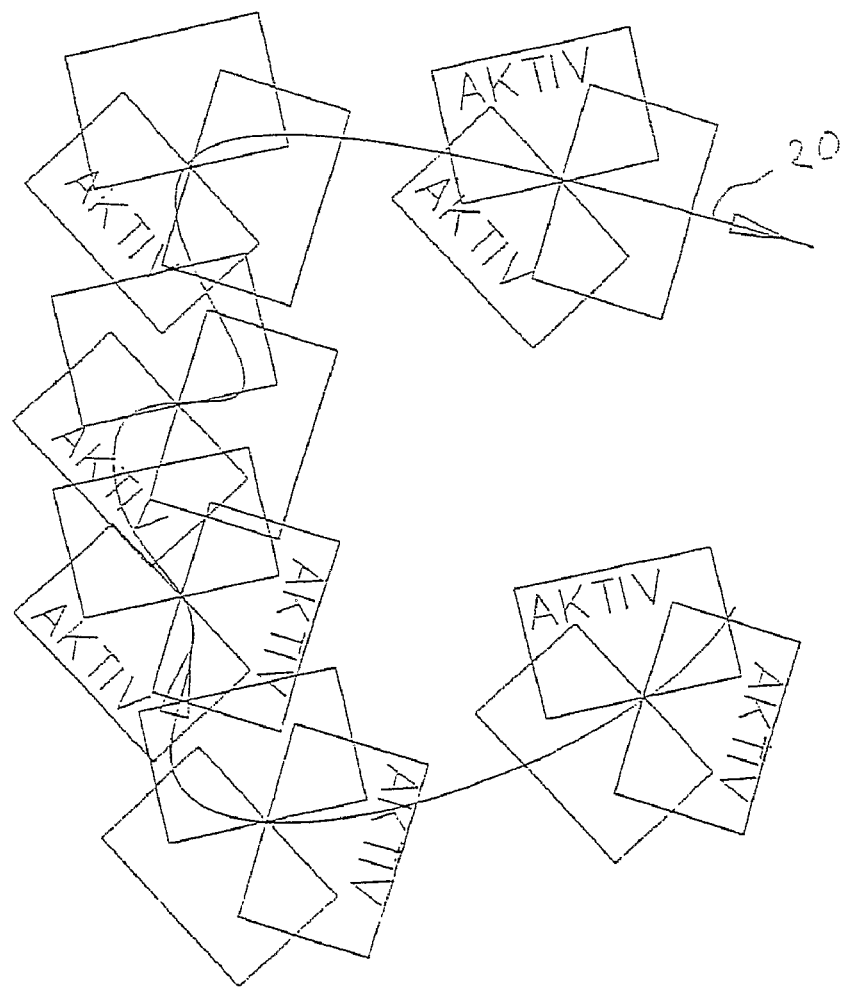
FIG. 4 shows another travel path of the apparatus according to the invention with regard to the switching of the relevant camera.

FIG. 4 illustrates another progression of an adhesive trail 20 that illustrates which field of view 23, 24 and 25 is active (e.g., marked at "active"). For example, FIG. 4 depicts which camera has the corresponding field of view shown as a rectangle 27 (e.g. marked as "active") while traveling along the adhesive trail 20 for quality control purposes. Moreover, at least a second camera is active in a leading direction for seam application guidance and/or the progression of the sealing agent track (not shown). However, the cameras indicated to be active are arranged in a trailing direction and are switched automatically according to the progression of the adhesive trail 20. Therefore, at least one camera is active at any time for seam application guidance and fine adjustment of the application facility according to the given reference contour in the leading direction, which is opposite to the trailing direction.

Figure 5:
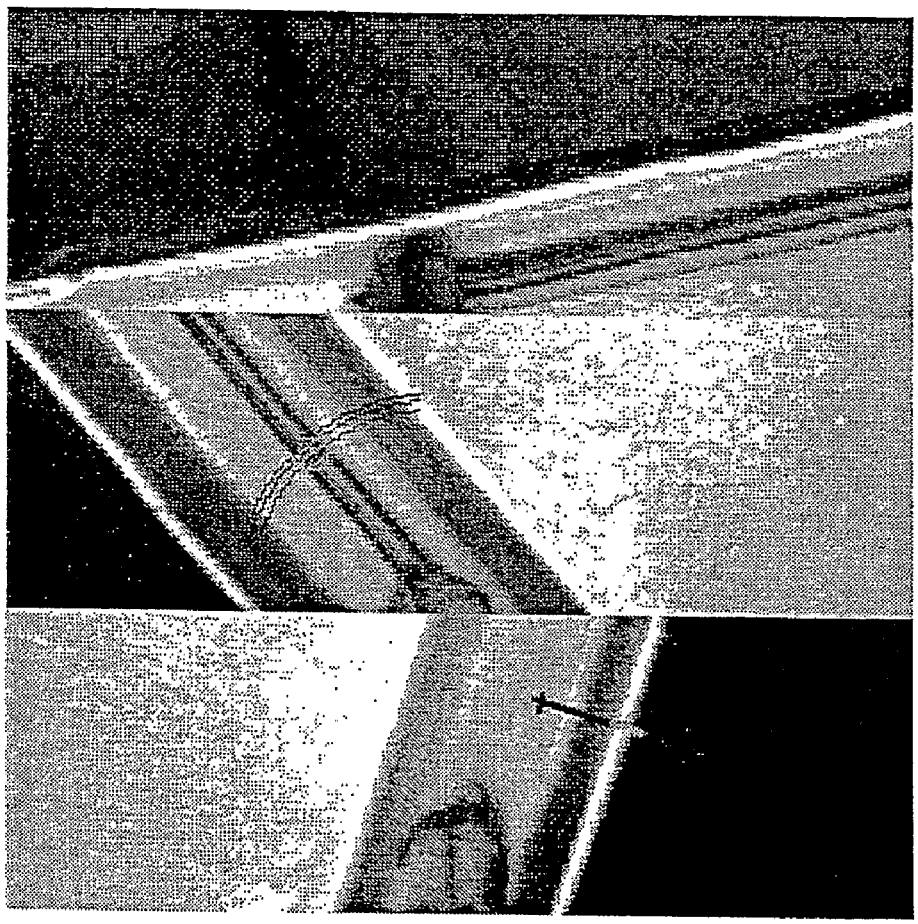
FIG. 5 is a view of a single image composed from three image strips from three cameras for seam application guidance and online monitoring of sealing agent application at one edge of a component.

FIG. 5 illustrates three image strips that each represent a relevant section and/or strip of an image of the three individual cameras 12, 13, and 14 of FIG. 1. According to the method of the invention, each camera 12, 13, and 14 records a strip of the image 32, 33, and 34 in order to reduce the amount of data such that the recording rate can be increased. These individual image strips 32, 33 and 34 of the three cameras 12, 13, and 14 are then joined into an image, whereby the image recording occurs at defined fixed time intervals and independent of the robot control of the application facility. For example, the cameras 12, 13, and 14 only record a strip of the image 32, 33 and 34. Instead of an image height of 480 pixels, an image height of approximately 100 pixels (100 image lines) is used. By means of this partial scanning technique (e.g. partial reading-out of the image recording chip), only small data streams are generated. Thus, the image recording rate can be increased several-fold. Synchronous image recording and parallel image capture allow the three image strips 32, 33 and 34, one below the other, to be composed into a single image. As a result, the three image strips 32, 33, and 34 are correctly arranged and assigned with regard to location and time relative to the travel path of the application facility 11 and without further delay and can be processed. Thus, the image recording technique facilitates simultaneous and parallel recording of individual camera images, increases the image recording rate both guidance or regulation of the application facility 11 and for online monitoring of the adhesive agent applied, whereby the images of all cameras 12, 13, and 14 are stored in a sequence of images.

Once the images of the three cameras 12, 13, and 14 are stored in a sequence of images, a parameterization of a reference track is carried out as the subsequent step of teaching-in the reference adhesive trail. The robot travel path, robot travel time, direction, width, and quality of the adhesive trail 20 are used in the parameterization. The parameterization results in a type of vector chain for the adhesive trail 20. The vector chain attains high image recording rates and comparably short partial sections (e.g., between 1 and 3 mm). Vectorization has another advantage in that the adhesive trail 20, being in the form of a vector chain, can be stored in a camera-transcending global coordinate system.

As is evident from FIG. 5 illustrates seam application guidance at an edge of a component, the seam inspection is carried out online in the middle strip of FIG. 5, whereby the segment of a circle is the area, in which the first camera provides for monitoring of the adhesive.

Application facilities or robots work with an internal interpolation clock time of 12 ms, for example. The regulation of seam application guidance according to the lower strip of FIG. 5 cannot occur more rapidly than this interpolation clock time. Therefore, at a maximal robot travel speed of 700 mm/s, the path traveled in 12 ms is 8.4 mm. Accordingly, if a correction value is determined at time point x, the correction can be made only at the next interpolation clock time (i.e. 8.4 mm after determination of the value). As a result, the reference edge must be captured at least 8.4 mm ahead of the nozzle. This area is covered by the arrangement of the optical sensor system and correction values are made available in due time by the rapid analytical cycle (e.g., <5 ms). Because the cameras 12, 13, and 14 are attached around the application facility 11 in a fixed position, the progression of the adhesive trail 20 changes. Thus, the seam correction can be carried out in the first strip according to the first camera, in the second strip according to the second camera or in the third strip according to the third camera. Consequently, as described above with regard to the online monitoring of adhesive application, another camera becomes active for seam correction when the reference seam migrates from the field of view of one camera into the field of view of another camera.

The bottom strip of FIG. 5 shows a bright cross on the line perpendicular to the edge of the component right at the edge of the component that is used as reference edge for seam application guidance. Paralleling this, the seam inspection for monitoring of sealing agent application is carried out in an online fashion in the middle strip 33 of FIG. 5.

If the adhesive trail 20 progresses out of the field of view of a camera, the adhesive trail 20 is transiently in the overlapping area of the ranges of angles of the two cameras. If the adhesive trail 20 then progresses from the segment of the circular line of the one camera via the overlapping area to the segment of the circular line of another camera, an automatic switch is made from the one camera to the other camera. This is shown, in particular, in FIG. 4 by means of the active fields of view 27 of the individual cameras.

The advantages mentioned above are attained by the individual cameras forming a circular caliper whose center is formed by the application facility 11, whereby the search for both the reference edge and the edges of the adhesive trail 20 proceeds on a circular line directly around the application facility 11. For this purpose, it is essential that the individual cameras 12, 13, and 14 are directed at the application facility 11, whereby the axial longitudinal axes of the individual cameras 12, 13 and 14 intersect the longitudinal axis of the application facility 11.

The illumination module (not shown here) for the apparatus according to the invention is made up of light emitting diodes (LEDs), in particular infrared LEDs, ultraviolet LEDs (UV LEDs) or red-green-blue LEDs (RGB LEDs). In order to attain as little movement or blur as possible and have a high contrast in image recording, the LEDs can be flashed. For example, short, strong pulses of current on the order of 1.0 to 0.01 ms can be applied to the diodes. In this context, light-emitting diodes capable of emitting light of various colors are particularly advantageous because the sensor design can be switched to other types of adhesives or other colors of adhesives without reconfiguration.

A teach-in run and/or a teach-in of a reference adhesive trail is illustrated in the following paragraphs below.

The teach-in process of the reference adhesive trail can be started by the user by marking the position of the adhesive trail 20. This is sufficient for fully automatic recognition of a position and a direction of the adhesive trail 20 in the subsequent camera images because the image recording rate is sufficiently high and the individual images are recorded very shortly after one another (e.g., every 1 mm to 3 mm). From the starting point, the adhesive is scanned image by image. The adhesive trail position and the adhesive trail angle detected in the current image are used for the upcoming image as a priori knowledge. The a priori knowledge facilitates fully automatic capture of the adhesive trail 20 without a human being having to determine or assess the image or the position of the adhesive trail 20. As a result, the search area can be limited and/or adjusted.

Figure 6:
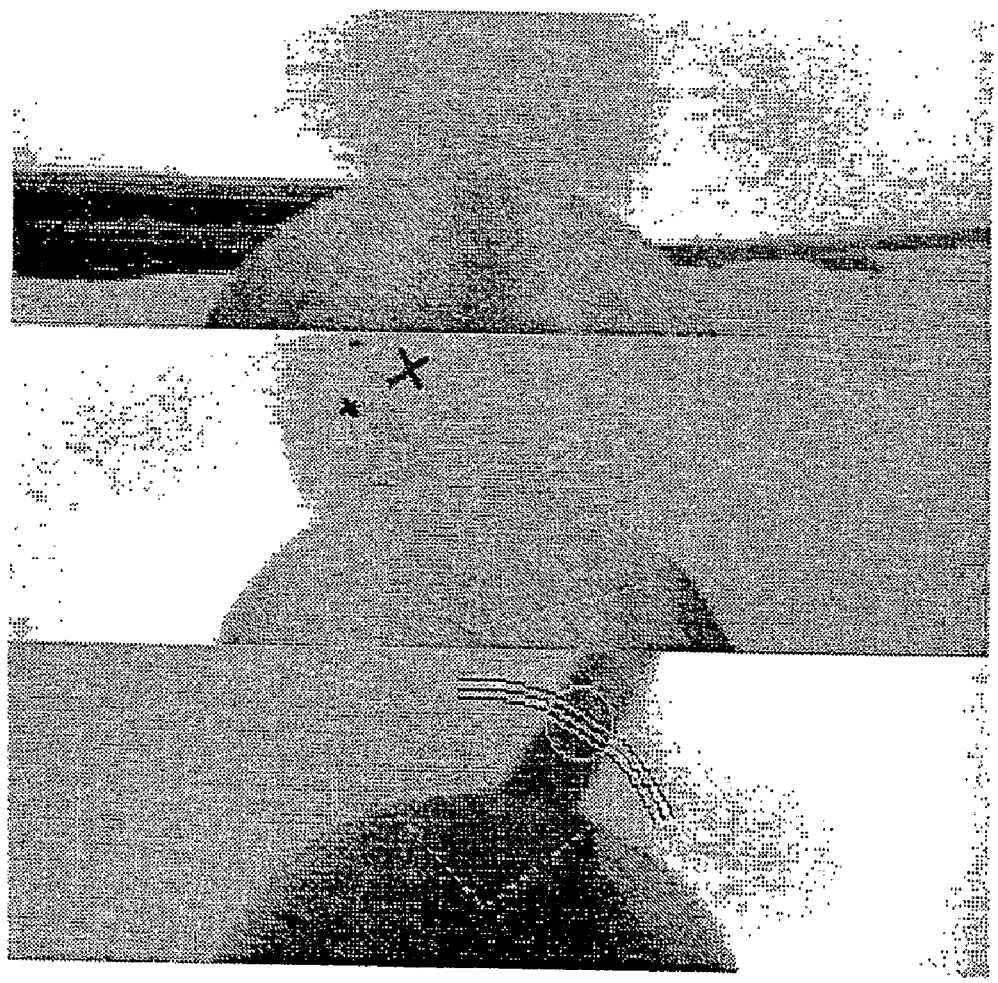
FIG. 6 is another view of a single image composed from three image strips from three cameras, whereby two overlapping components are being glued together.

FIG. 6 illustrates a guidance of a seam application in the overlapping area of two components, particularly at a place where the two components abut. The second camera shows the strip of the second camera read-out according to a partial scanning method, in which the position of the overlap of the two metal sheets is determined as a reference contour or a reference edge to guide the seam application. The strip of the third camera, in which the applied sealing agent track is monitored in parallel to seam application guidance, is shown in the bottom strip of FIG. 6. For this purpose, the segment of a circle is shown in the bottom strip, in the middle of which progresses the adhesive trail 20 as indicated by a circle. The image recording strip of the first camera 14 is shown in the top strip of FIG. 6.

Figure 7:
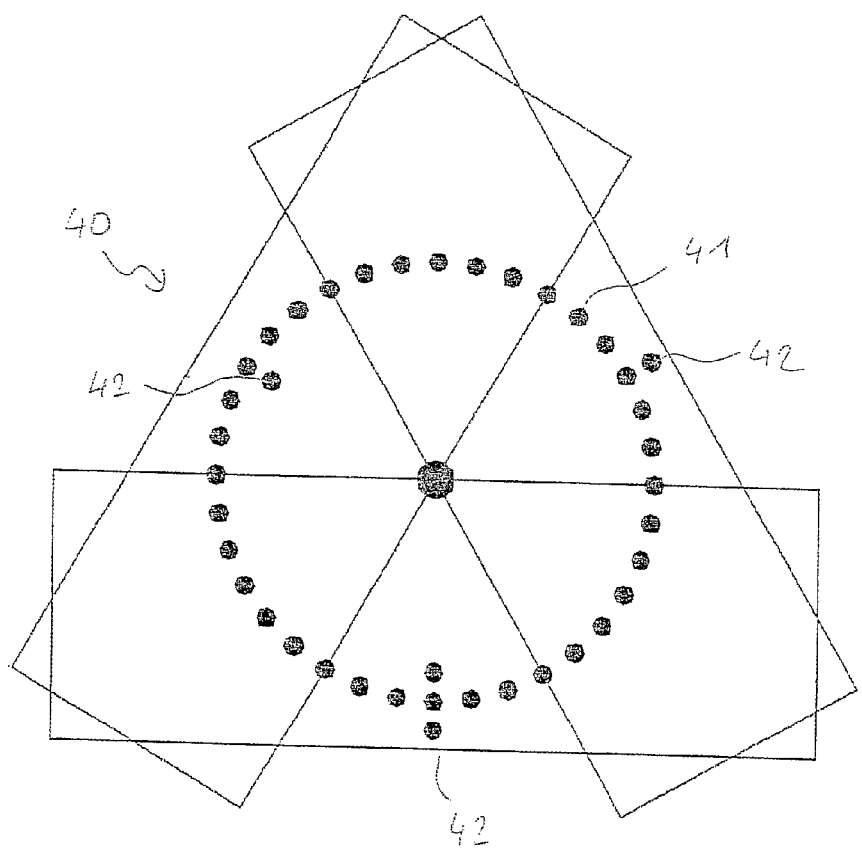
FIG. 7 shows a schematic view of a calibrating device according to the invention for calibrating the individual cameras of the apparatus according to the invention for automatic application and monitoring of a structure to be applied onto a substrate.

FIG. 7 illustrates a calibration facility 40 in the form of a circular calibrating disc. The calibration facility 40 assigns to the individual cameras 12, 13 and 14 a scaling factor, an angle assignment, and the center and radius of the search circle. The calibrating disc consists of individual form elements, shown as dots 41, that are arranged on a circular line. The form elements are spaced at an angle distance of essentially 10° from one another. Moreover, marker sites 42 are arranged at equal distance from each other in order to calibrate the three cameras 12, 13, and 14. A compensation calculation is determined by utilizing the coordinants of the centers of the individual dots, the scaling factors of the individual cameras 12, 13 and 14 and, the center and radius of the search area. The marker sites are located at angles of 0°, 120°, 240° in the global coordinate system allowing the angle assignment and the corresponding fields of view of the individual cameras 12, 13, and 14 to be determined. The field of view for the individual cameras 12, 13, and 14 are indicated by the three rectangles 43, 44, and 45 shown in FIG. 7. The form elements 41 can correspond to the circular line of the circular caliper for detection of the adhesive trail 20.

Figure 8:
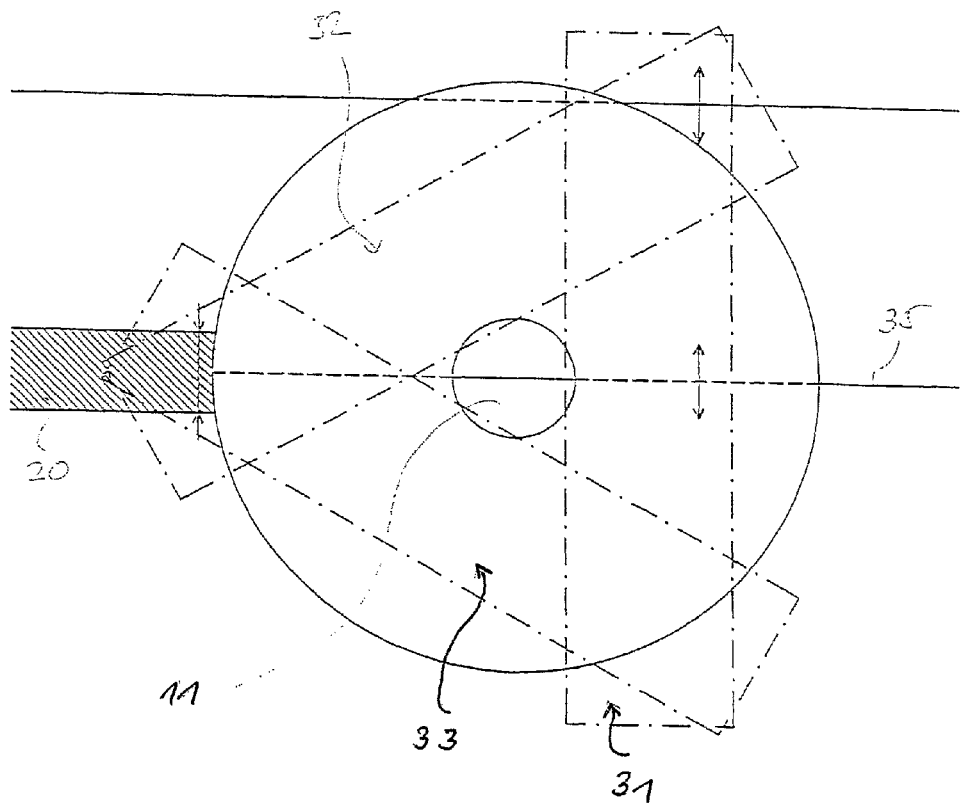
FIG. 8 shows a top view with regard to the basic principle of seam tracing.

FIG. 8 illustrates three strips around the application facility 11 each by dashed lines that represent the read-out area for the partial scan of the individual cameras 12, 13, and 14. The strip 31 of the first camera determines the reference edge 35 that controls and/or regulates the application facility 11 according to the progression of the reference edge. Image strip 31 is facing in a leading direction and measures the position of the reference edge and/or fold 35 such that the application facility 11 applies the sealing agent onto the track correctly according to reference contour 35. After correction of a robot track with regard to a coachwork position, the joining seam is recognized by driving to a first position and activating a seam application guidance. After release of the process (e.g., a seam is recognized), the robot track continuously receives correction values that are perpendicular to the application direction taught-in. In this context, a capture area can be ±15 mm, whereby a regulation area is <±1 mm. The communication between the image processing system and the robot system and/or application facility proceeds, for example, by means of a standardized Ethernet interface using an XML protocol. In the trailing direction, the two image strips 32 and 33 intersect in the area of the sealing agent track 21.

The online monitoring of an applied adhesive trail shall be illustrated briefly in the following paragraphs. The application facility 11 shown in FIG. 1 applies the adhesive trail 20 onto the metal sheet 31. The application facility 11 is moved jointly with the cameras 12, 13, and 14 over the metal sheet 31 and regulated according to the reference contour. However, a kinematic inversion is also feasible, for example, the metal sheet 31 being moved and the application facility 11 with the cameras 12, 13, and 14 being arranged to be fixed in position. The applied adhesive trail 20 is determined and analyzed synchronously and in parallel by one of the cameras 12, 13, 14 on the circular line of the circular caliper (shown in FIG. 5). Each camera 12, 13, and 14 records only a strip of the image 32, 33, and 34 and joins these into a single image. The image recording rate is increased in accordance with the data reduction attained because each camera 12, 13, and 14 records only a strip of the image 32, 33, and 34. The individual image strips 32, 33, 34 in the joint image facilitate the synchronous, parallel, as well as simultaneous capture of the three camera images. The individual images of the three cameras 12, 13, and 14 can be assigned directly as a function of location. As a result, seam application guidance and online monitoring of the adhesive trail 20 in real-time is feasible and achieves high accuracy at high travel speeds because of the high image recording rate both in the regulation according to the reference edge and in the inspection of the applied adhesive trail 20.

Figure 9:
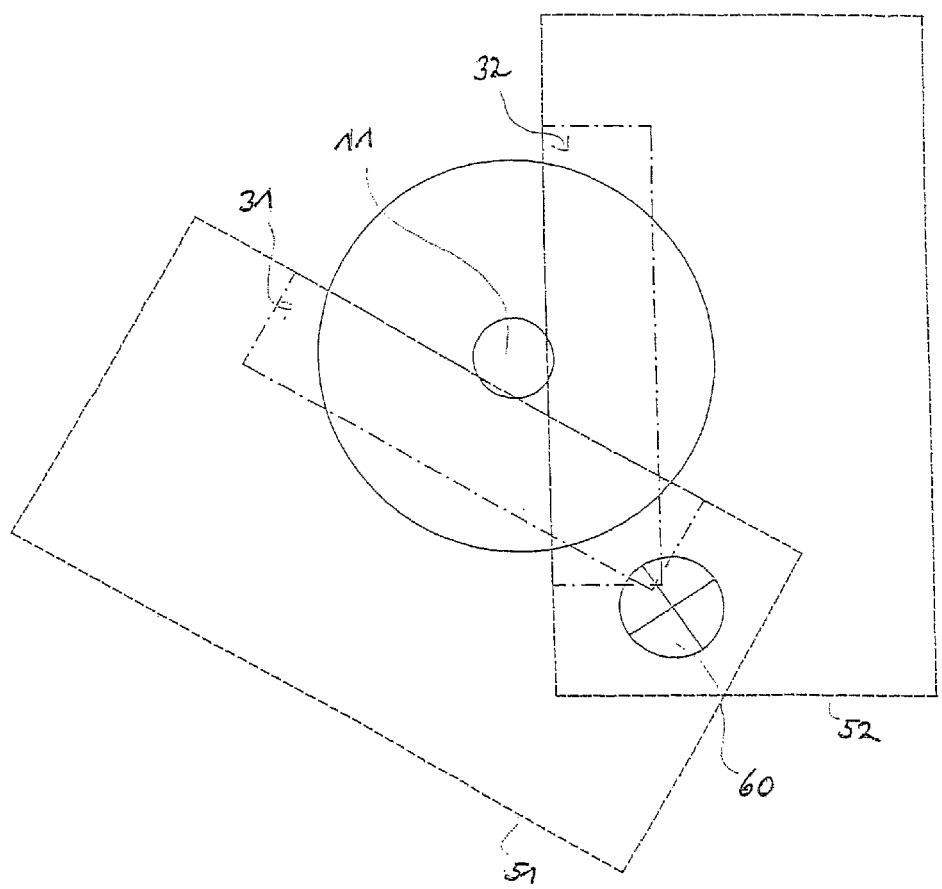
FIG. 9 shows a top view with regard to the principle of 3D positional recognition.

FIG. 9 illustrates the basic principle of 3D positional recognition that is carried out prior to applying a sealing agent. Because the metal sheets 31, for example raw coachwork of vehicles, are not always positioned in exactly the same position by the supplier of the technology and the position of the joining seams is associated with tolerances, gross adjustment and/or gross positioning of the apparatus according to the invention is an advantage. For this purpose, the camera image fields are switched to a large image, a standard size, or a full image, which is indicated for each particular case by the dashed lines 51 and 52. The standard camera image field 51 shows the expanded field of view of a camera reading the corresponding strip 31 according to the partial scanning procedure. The strip 32 is scaled down analogous to strip 52 and according to the ratio of the standard camera image field 52. For example, the image strip 31 or 32 is scaled down by software, for example, to half the width and ⅓ of the height of the image fields 51 and 52. For reasons of clarity of presentation, the corresponding standard camera image field 53 with corresponding image strip 33 is not shown. In the 3D positional recognition, an arbitrary feature 60 within the overlapping field of view of the two camera image fields 51 and 52 is measured. Since the two camera image fields 51 and 52 overlap in the area of feature 60, the procedure of stereometry can be used to facilitate a three-dimensional analysis, for example, of a hole or an edge of the component. If, for example, a seam of two components has been recognized, the application facility 11 can carry out an automatic correction of position through the help of the sensory system in order to carry out the correction of the robot track and/or application facility track in an online fashion, as described in FIG. 8. The sensory system can carry out at the same time the quality control of seam sealing in an online fashion, as described in FIG. 8. The 3D positional recognition provides for positional correction of the application facility 11 and online regulation of the progression track of the application facility 11 as well as online monitoring of sealing agent application with a single sensory system that is configured, for example, with three cameras 12, 13 and 14 in a fixed position arranged around the application facility 11. In this context, a strip of the image 31, 32, 33 is recorded according to the invention in order to utilize small data streams to achieve an increase in the image recording rate. The use of the partial scanning technique thus provides for an image refresh rate of approximately 240 Hz or less. The images are therefore recorded at defined fixed time intervals and are independent of the speed of the robot and the application facility 11. In addition, a frame grabber board (e.g., a personal computer (PC) board for capturing images from the camera) is used in the analytical PC allowing images from all three cameras 12, 13, and 14 to be captured synchronously and in parallel. The images are subsequently composed into one image (i.e., 3 strips one below the other) providing the advantage of three images each being directly assigned accordingly in a location-dependent fashion.

Moreover, it is sufficient, in particular, to search for and analyze, for example, the sealing agent track in one of the three images. If the angle value exceeds a certain value, an automatic switch to the neighboring camera is made. In this context, the angle value refers to a full circle of 360°, which results in a global coordinate system. Each camera comprises an area of overlap with the next camera. The selection of the camera is made independent of the position of the application facility 11, robot position, and a time component, but rather always refers to the actual inspection results which are captured in the global coordinate system. This prevents errors that are generated by the relative inaccurate robot controls and application facility 11 controls.

Figure 10:
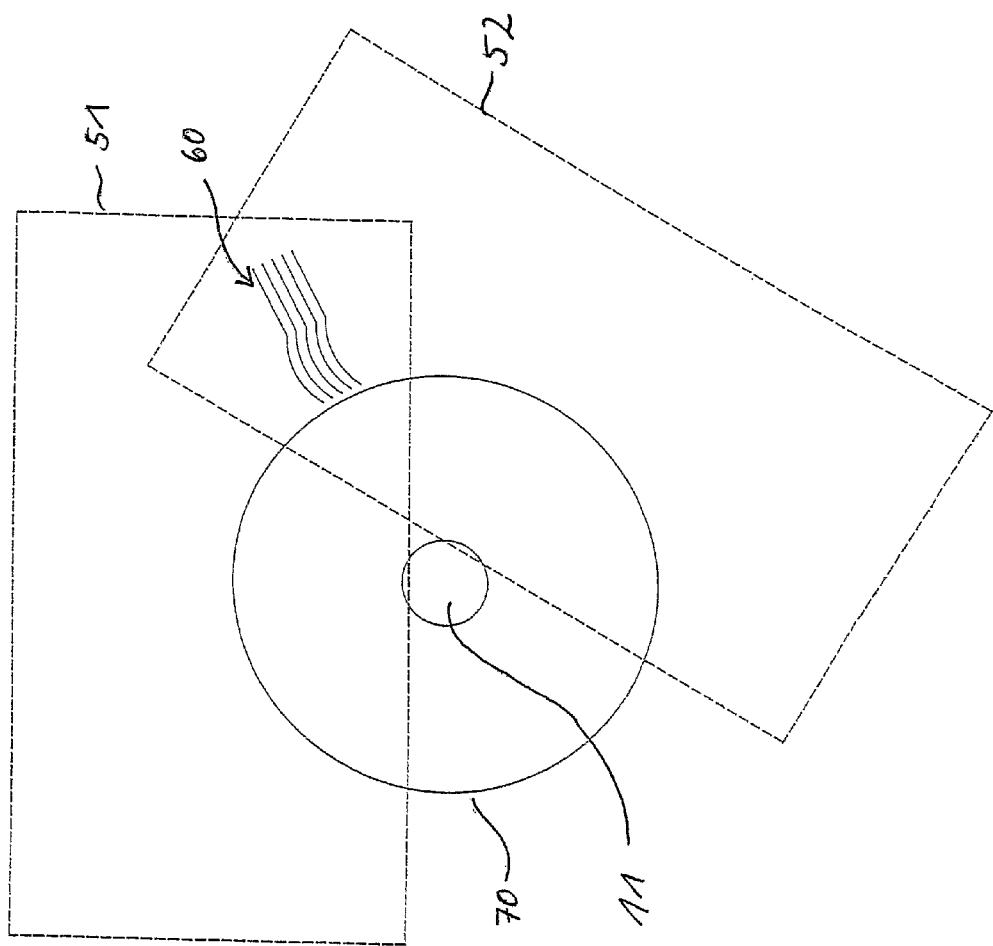
FIG. 10 shows a top view with regard to profile analysis.
Figure 11:
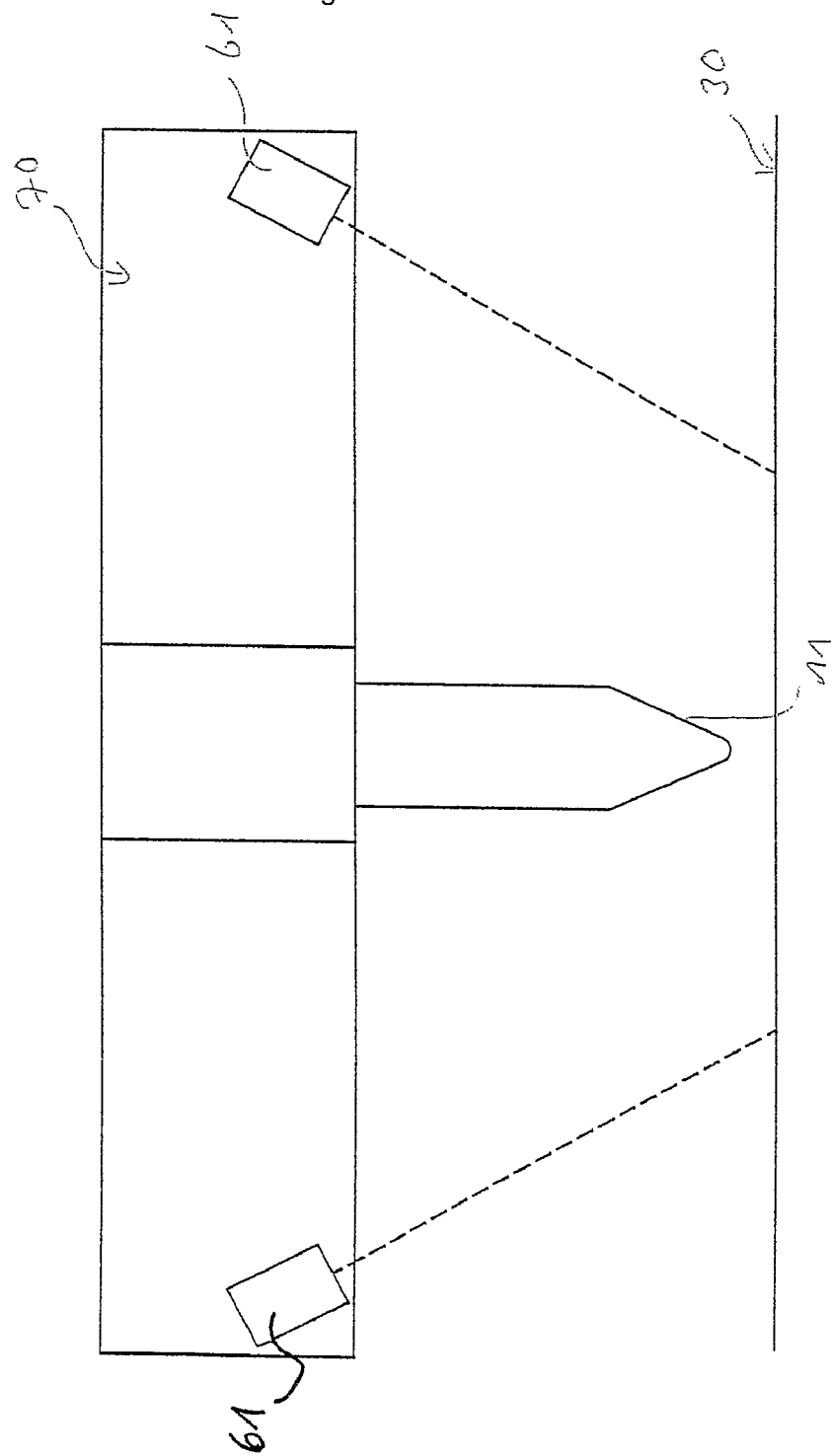
FIG. 11 is a schematic side view of the apparatus according to the invention with projection facility.

The three-dimensional profile analysis by means of a projection is described according to FIGS. 10 and 11. FIG. 10 illustrates by dashed lines two camera fields of view 51, 52. In the overlapping area of the two camera fields of view 51, 52 are shown a plurality of laser lines 60 that are used for a profile analysis with regard to the width and contour of structure lines and for generation of soft contours. The laser lines 60 are generated by a projection facility that can, for example, be arranged on the optical sensor with three cameras. Moreover, the projection facility can be arranged directly on the application facility 11. The sensor with the three cameras is shown schematically by the circle 70. The laser lines 60 or laser strips are projected onto the component 32 or metal sheet 31 highlighting contours on the component 30 that cannot be used for a three-dimensional analysis by conventional image processing. Artificial features are generated by means of the laser lines 60 on the component 32 and can subsequently be analyzed by means of image processing according to stereometry. Thus, FIG. 10 shows the principle of three-dimensional positional recognition prior to the application of the sealing agent in case no hard, analyzable features are present. In contrast, a hard contour is described by means of feature 60 as illustrated by FIG. 9 and as described above.

FIG. 11 illustrates a side view of the application facility 11 with a sensor unit 71. The sensor unit 71, aside from the three cameras, can comprise at least two projection facilities 61 that project laser lines onto the metal sheet 31 or the substrate 30, as shown schematically by the dashed line 62. Arranging multiple projection facilities 61 around the application facility 11 allows a gap-free contour to be generated on the metal sheet 31. The gap-free contour can be used for three-dimensional analysis because the sensor 71 and the projection facility 61 are calibrated. Accordingly, FIG. 11 shows two projection facilities 61 in an exemplary fashion. Projection facilities 61 of this type can, for example, project a laser onto the substrate or the component. In addition, projection facilities 61 can have an LED module comprising an adapter lens to generate a line on the substrate.

Figure 12:
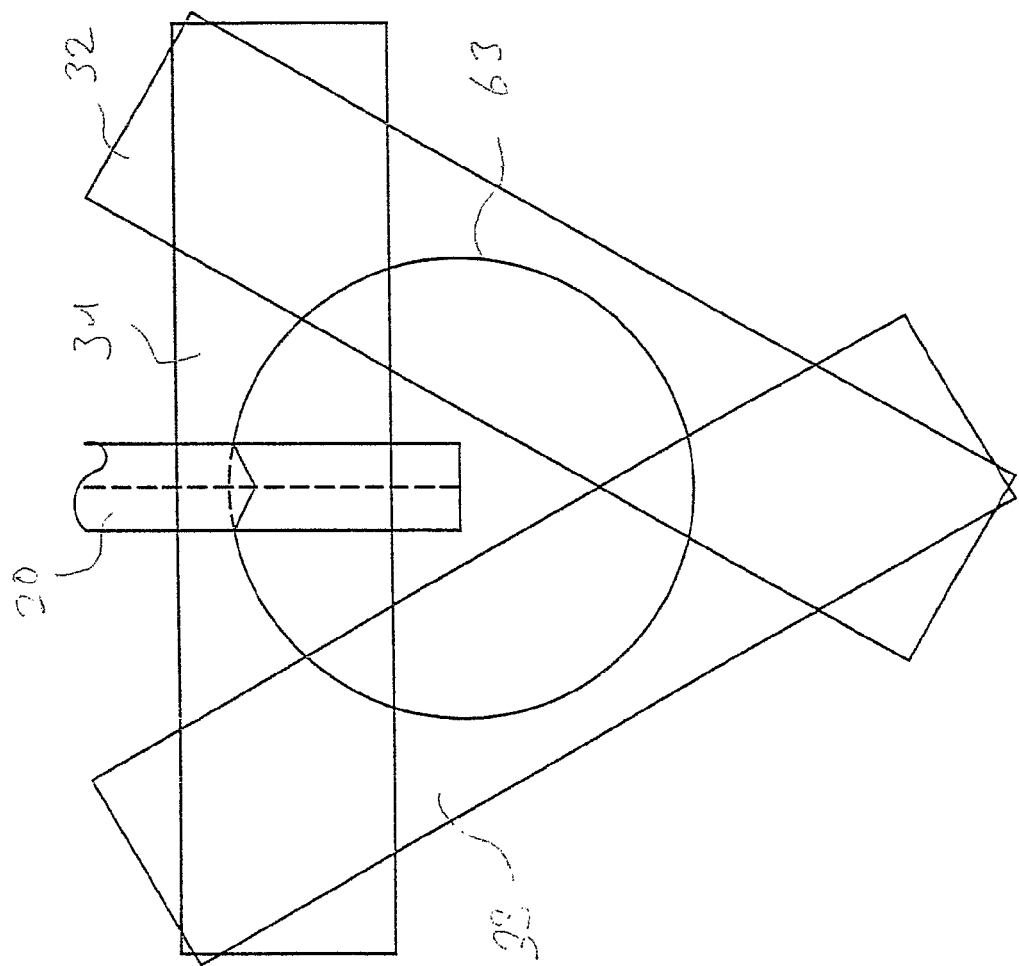
FIG. 12 is a schematic top view of a projection applied to be circular.

The projection facilities 61 can be used both for three-dimensional positional correction prior to sealing agent application as well as for online analysis of a height and a profile of the applied sealing agent. For three-dimensional positional correction, the projection facilities 61 can, preferably, project multiple lines. For height analysis, one or more projection facilities 61 should be provided that project a line or, as shown in FIG. 12, a circular contour onto the component and/or substrate. Multiple lines can be advantageous for the analysis.

FIG. 12 illustrates to determine sealing agent height and/or sealing agent contour and sealing agent position according to the principle of triangulation by means of the image processing simultaneously directly after sealing agent application. A round contour 63, for example, is applied to the metal sheet 31 by the projection facilities. The sealing agent 20 or the sealing agent track 21 provides for a change of height and position of the projected contour 63. The round projection contour 63 thus changed is determined by the individual object fields of the individual cameras 12, 13 and 14. Thus, the original shape of the projected contour 63 is deformed by the sealing agent 20 such that the width, contour, but also the height and position of the applied sealing agent 20 can be determined according to the principle of triangulation. In the principle of triangulation, there is a defined angle between the camera and the projection facility 61, whereby the camera and the projection facility 61 are calibrated with respect to each other. Because of the angle, the substrate contours illuminated by the projection facility appear in different positions on the light-sensitive chip and/or charge-coupled device (CCD) chip or complementary metal oxide semiconductor (CMOS) chip as a function of their height such that the height and contour of the sealing agent can be calculated due to the calibration of the camera and projection facility 61.

According to an embodiment that is not shown here, the sensor 71 that is configured with three cameras 12, 13, and 14 arranged around the application facility 11, which is configured such that the optical axes of the individual cameras 12, 13, and 14 are directed to be parallel to each other. The cameras 12, 13, and 14 are, perpendicular to the substrate 30 or metal sheet 31. An arrangement of this type allows the sensor 71 to be arranged particularly close to the area of sealing agent application, whereby the fields of view of the individual cameras 12, 13, and 14 comprise an overlapping area whose size depends on their wide angle.

The invention claimed is:

1. A method for automatic application and monitoring of a structure to be applied onto a substrate, the method comprising:
   determining a reference contour by utilizing a first camera in a leading direction to record a plurality of images;
   regulating the progression of the structure to be applied according to the reference contour;
   guiding an application facility based on the images recorded by the first camera;
   applying the structure onto the substrate by the application facility according to the reference contour determined by the first camera; and
   monitoring the structure applied onto the substrate by the application facility utilizing a second camera in trailing direction;
   wherein the method is performed such that the cameras have an overlapping area on a circular line, a segment of the circular line is assigned to images of each camera, at least one of the reference contour and the applied structure progresses relative to the cameras from one camera to the next camera, and an automatic switch is made when the applied structure or the reference contour progresses relative to the cameras from the segment of the circular line of one camera via the overlapping area to the segment of the circular line of another camera.

2. The method according to claim 1, wherein the structure comprises at least one of an adhesive line and an adhesive trail.

3. The method according to claim 1, wherein the reference contour comprises a reference edge of a component that is to be joined to the substrate.

4. The method according to claim 1, wherein the two cameras record an image of at least one of the substrate, a section of a component to be joined to the substrate, and one or more components, the image including at least one of an image strip, a full image, and a large image.

5. The method according to claim 2, wherein the overlapping area is in the leading direction.

6. The method according to claim 5, wherein the overlapping area recognizes the reference contour as a three-dimensional reference contour, and a position of the reference contour is used to adjust the application facility prior to applying the structure.

7. The method according to claim 1, wherein a projection is made onto an area of the reference contour for three-dimensional analysis.

8. The method according to claim 7, wherein the projection comprises at least one laser line applied onto the substrate.

9. The method according to claim 1, wherein at least one camera records each of one or more images as an image strip for at least one of an online regulation of the application structure and an online monitoring of the applied structure.

10. The method according to claim 1, wherein the second camera records an image strip, and the second camera uses the image strip for online monitoring of the applied structure.

11. The method according to claim 1, wherein the method is performed such that the first and second cameras each record images as image strips, and the image strips of the two cameras are recorded to form a single sequence of images.

12. The method according to claim 9, wherein an image recording rate is increased in proportion with data reduction achieved by recording each image as an image strip.

13. The method according to claim 9, wherein a particular image comprises a plurality of picture lines, each camera utilizing at least one of a third, a fourth, and a fifth of the picture lines as a strip of the image.

14. The method according to claim 13, wherein an image recording rate of the cameras is multiplied by at least one of a three-fold, a four-fold and a five-fold factor based on the plurality of picture lines utilized.

15. The method according to claim 1, wherein a parameterization and a recording of an application track proceed in a single image recording run, whereby the images of all cameras are stored in a sequence of images.

16. The method according to claim 15, wherein the parameterization is determined by the stored sequence of images of at least a robot travel path, a robot travel time, robot coordinates, a position of the applied structure, a contrast of the applied structure, a gray scale value of the applied structure, a color value of the applied structure, a width of the applied structure, and a quality of the applied structure.

17. The method according to claim 16, wherein the parameterization is stored as a vector chain.

18. The method according to claim 17, wherein the vector chain comprises a plurality of images recorded at a high image rate.

19. The method according to claim 18, wherein the vector chain comprises a plurality of images recorded as short partial sections, the sections being less than 4 mm in length.

20. The method according to claim 19, wherein the vector chain comprises sections between 0.5 mm and 4 mm in length.

21. The method according to claim 19, wherein the vector chain comprises sections between 1 mm and 3 mm in length.

22. The method according to claim 11, wherein the method is performed with a third camera, each camera being configured to regulate in a leading direction according to the reference contour and being configured for monitoring the applied structure in a trailing direction.

23. The method according to claim 22, wherein the three cameras each comprise an overlapping area to an adjacent camera on the circular line.

24. The method according to claim 23, wherein angle values of the circular line range from 0 to 360° and form a global coordinate system, and wherein a segment of the circular line is assigned to images of the third camera.

25. A method for automatic application and monitoring of a structure to be applied onto a substrate, the method comprising:
    determining a reference contour of a component to be connected to the substrate by utilizing a first camera in a leading direction to record a plurality of images;
    regulating the progression of the structure to be applied according to the reference contour;
    guiding an application facility based on the images recorded by the first camera;
    applying the structure onto the substrate by the application facility according to the reference contour determined by the first camera; and
    monitoring the structure applied onto the substrate by the application facility utilizing a second camera in trailing direction;
    wherein the method is performed with a third camera, each camera being configured to regulate in a leading direction according to the reference contour and to monitor the applied structure in a trailing direction, and the three cameras each comprise an overlapping area to an adjacent camera on a circular line, and wherein the method is performed such that at least one of the reference contour and the applied structure progresses relative to the cameras from one camera to the next camera, and an automatic switch is made when the applied structure or the reference contour progresses relative to the cameras from the segment of the circular line of one camera via the overlapping area to the segment of the circular line of another camera.

26. An apparatus for automatic application and monitoring of a structure to be applied onto a substrate, the apparatus comprising:
    at least one illumination module;
    an application facility for applying the structure onto the substrate; and
    a sensor unit having two cameras provided around the application facility, the two cameras including a first camera configured in a leading direction for regulation of the application facility by means of a reference contour and a second camera configured in a trailing direction for simultaneous online monitoring of the structure applied onto the substrate;
    wherein the cameras are configured such that the cameras have an overlapping area on a circular line, a segment of the circular line is assigned to images of each camera, and an automatic switch is made when the applied structure or the reference contour progresses relative to the cameras from the segment of the circular line of one camera via the overlapping area to the segment of the circular line of another camera.

27. The apparatus according to claim 26, wherein each camera has an optical axis, and the optical axes of the cameras are configured to intersect along a direction of view.

28. The apparatus according to claim 27, wherein the optical axes are configured to be at least one of the following: directed along a longitudinal axis of the application facility, parallel to each other, and perpendicular to the substrate.

29. The apparatus according to claim 26, wherein the sensor unit further includes a third camera.

30. The apparatus according to claim 29, wherein the first, second and third cameras are arranged at equal distances from each other in a circle.

31. The apparatus according to claim 26, wherein the cameras are configured to interact with each other such that the images of the cameras are stored in a sequence of images.

32. The apparatus according to claim 31, wherein each camera is configured to record each associated image as an image strip to form a part of the sequence of images.

33. The apparatus according to claim 26, wherein a recording rate is increased according to data reduction achieved by recording each image as a single strip.

34. The apparatus according to claim 26 further comprising a projection facility provided on the application facility, the projection facility being configured to project a plurality of image strips onto the substrate for a three-dimensional analysis.

35. The apparatus according to claim 34, wherein the projection facility is configured to emit at least one laser line for a three-dimensional profile analysis.

36. The apparatus according to claim 26 further comprising at least two projection facilities arranged around the application facility, the at least two projection facilities being configured to project a plurality of image strips onto the substrate for a three-dimensional analysis.

37. The apparatus according to claim 26, wherein the cameras are directed at a circle whose center coincides with a center of the application facility, and wherein the cameras are configured to perform at least an essentially circular edge scan in the form of a circular caliper.

38. The apparatus according to claim 37, wherein the sensor unit further includes a third camera and each individual camera is configured to image at least one of an overlapping area between 30° to 90° and an overlapping area of approximately 60° relative to the next camera.

39. The apparatus according to claim 26, wherein the at least one illumination module comprises light emitting diodes (LEDs), and the LEDs comprise at least one of an infrared LED, an ultra-violet (UV) LED, and a red-green-blue (RGB)LED, and wherein the LEDs are configured to flash utilizing pulses of current ranging between 1.0 to 0.01 ms.

40. The apparatus according to claim 29, wherein the apparatus further comprises a calibrating device having individual form elements spaced apart at an angle distance of 10° to calibrate the individual cameras for assignment of an angle assignment.

41. The apparatus according to claim 40, wherein the calibrating device further comprises at least three marker sites utilized to calibrate the three cameras, the marker sites being arranged in a circular arc of the calibrating device and located at approximately 0°, 120°, and 240°.

42. The apparatus according to claim 41, wherein the marker sites are formed by at least two form elements, and the marker sites are located on the circular arc extending to an angle range of approximately 10°.

43. The method of claim 1 wherein the structure comprises a sealing agent.

44. The method of claim 1 wherein the reference contour is determined by performing a three-dimensional positional correction for the application facility by means of a stereometry procedure utilizing the first and second cameras.

45. An apparatus for automatic application and monitoring of a structure to be applied onto a substrate, the apparatus comprising:
at least one illumination module;
an application facility for applying the structure onto the substrate;
a sensor unit having multiple cameras provided around the application facility, the multiple cameras including a first camera configured in a leading direction for regulation of the application facility by means of a reference contour, a second camera configured in a trailing direction for simultaneous online monitoring of the structure applied onto the substrate, and a third camera; and
a calibrating device having individual form elements spaced apart at an angle distance of 10° to calibrate the individual cameras for assignment of an angle assignment, wherein the calibrating device further comprises at least three marker sites for calibrating the three cameras, the marker sites being arranged in a circular arc and located at approximately 0°, 120° and 240°.

* * * * *